United States Patent [19]

Torck et al.

[11] Patent Number: 4,664,675
[45] Date of Patent: May 12, 1987

[54] PROCESS FOR UPGRADING OLEFINIC GASOLINES BY ETHERIFICATION

[75] Inventors: Bernard Torck, Boulogne Sur Seine; Pierre Amigues, La Muladiere; Jérôme Weill, Lyons; Claude Gueguen, Irigny; Michel Llinares, Saint Genis Laval; Henri Bourgognon, Tassin La Demi-Lune, all of France

[73] Assignees: Institut Francais du Petrole, Rueil-Malmaison; Elf France, Paris, both of France

[21] Appl. No.: 745,985

[22] Filed: Jun. 18, 1985

[30] Foreign Application Priority Data

Jun. 18, 1984 [FR] France ............................. 84 09623

[51] Int. Cl.⁴ .............................................. C10L 1/10
[52] U.S. Cl. .......................................... 44/60; 44/53; 44/56; 568/697; 568/699
[58] Field of Search ............... 44/60, 53, 56; 568/697, 568/699

[56] References Cited

U.S. PATENT DOCUMENTS

| 3,037,052 | 5/1962 | Bartnick | 568/335 |
| 4,118,425 | 10/1978 | Herbstmann | 568/678 |
| 4,193,770 | 3/1980 | Chase et al. | 44/53 |
| 4,204,077 | 5/1980 | Woods et al. | 568/699 |
| 4,218,569 | 8/1980 | Chase et al. | 568/699 |
| 4,544,776 | 10/1985 | Osterburg et al. | 568/699 |

FOREIGN PATENT DOCUMENTS 1153395 6/1983 Canada ............................... 260/648

Primary Examiner—Ferris H. Lander
Assistant Examiner—Margaret B. Medley
Attorney, Agent, or Firm—Millen & White

[57] ABSTRACT

The invention concerns a process for upgrading olefinic gasolines containing $C_5$ hydrocarbons, but free of $C_4$ hydrocarbons, by etherification. It is characterized in that the tertiary olefins of the charge are reacted (1 and 2) with methanol; the reaction effluent being then extracted (3) with water, in order to separate an aqueous phase containing the major part of the unreacted methanol from a hydrocarbon phase containing the major part of the formed ethers. The aqueous phase is then introduced in a distillation zone (4) where water is separated from methanol and recycled to the extraction zone (3), whereas methanol is recycled to the etherification zone (1 and 2).

11 Claims, 1 Drawing Figure

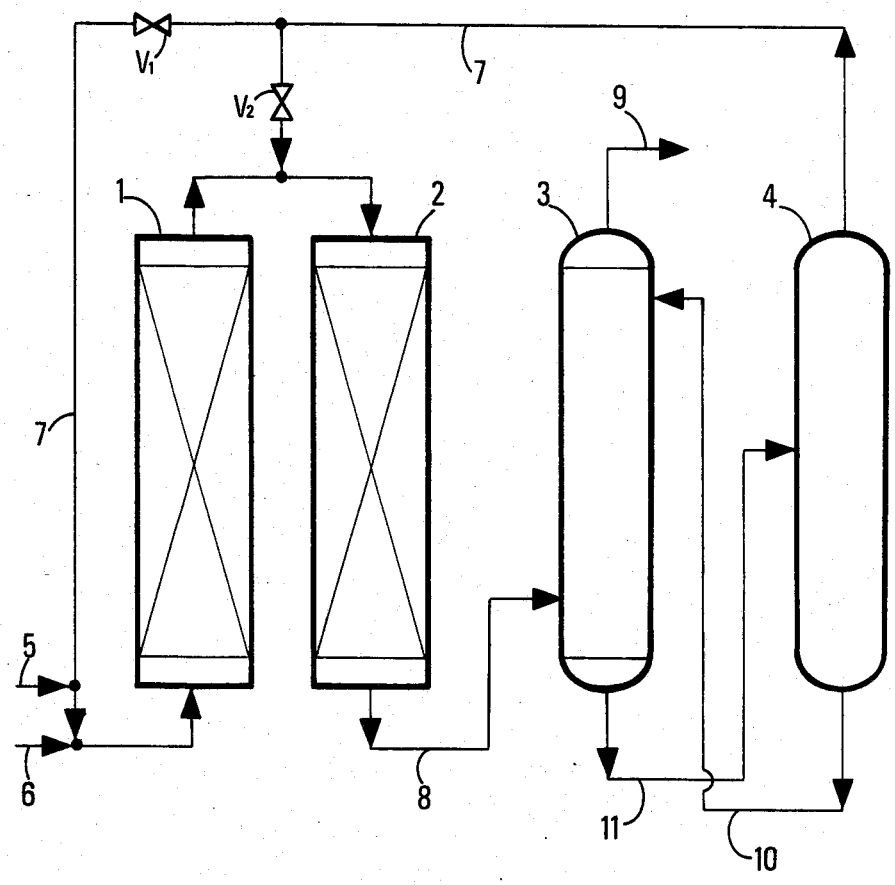

PROCESS FOR UPGRADING OLEFINIC GASOLINES BY ETHERIFICATION

BACKGROUND OF THE INVENTION

In the composition of a gasoline pool, the olefinic gasolines issued from cracking, visbreaking or coking units, form a substantial part of motor gasolines. However, generally these olefinic gasolines have relatively low octane numbers, and it has been suggested to increase their octane number by etherification of certain of their olefins with methanol. As a matter of fact, the light fraction of these olefinic gasolines contain tertiary olefins such as isoamylenes, isohexenes and isoheptenes which may easily react with alcohols such as methanol to give methyl ethers.

This etherification is generally performed with acid catalysts and more particularly with ion-exchange resins such as sulfonic resins.

The treatment of these gasolines with methanol in the presence of sulfonic resins provides an increase in their octane number and, in addition, decreases their olefin content, mainly tertiary olefin content, making it possible to upgrade methanol to premium gasoline without the problems arising when methanol is directly introduced in the gasolines, increases in the vapor pressure of the gasoline and phase separation when water is introduced in the storage tanks and the distribution circuits.

It is for this last reason that regulations in many countries do not allow the introduction of free methanol in gasolines except in the presence of co-solvents which eliminate separation problems.

The reaction between methanol and tertiary olefins is balanced and it is generally difficult to obtain conversion rates close to 100%. The conversion rate of the tertiary olefins is further reduced as the molecular weight of the olefin is increased.

Thus, whereas conversion of isobutene may be as high as 93 to 98% by mere passage over the catalyst, the conversion rate of isoamylenes, as described in French Pat. No. 2 411 881, in conditions similar to those used for producing methyl-tert butyl ether (MTBE), are at most about 50 to 60%. This patent shows that by recycling to the reactor a part of the light fraction containing the unreacted isoamylenes obtained by distillation of the reactor effluent, it is then possible to obtain a maximum conversion rate of about 70%, under operating conditions, reasonably economical in view of the high cost of the distillation.

Such a process flowsheet does not provide for the removal of the methanol excess remaining in the reactor effluent and which is hence found in major part in the free state in gasoline.

In order to completely remove the methanol excess contained in the mixture obtained by etherification of a mixture containing $C_4$ and $C_5$ tertiary olefins, it has been suggested, in the U.S. Pat. No. 4,204,077, to remove the methanol from the reactor effluent by extraction with such a solvent as ethylene glycol.

The authors of said patent consider that this solvent is preferable to water, which, during methanol extraction, drives along therewith a portion of the ethers contained in the reactor effluent.

SUMMARY OF THE INVENTION

The present invention has as an object the production of a $C_5^+$ hydrocarbon cut of high octane number from olefinic cuts.

This process for upgrading olefinic cuts containing hydrocarbons of 5 carbon atoms and more per molecule, particularly isoamylenes, and containing an insubstantial amount of hydrocarbons having 4 carbons atoms, i.e. less than about 5% by weight and preferably less than 1% by weight with respect to the total weight of the cut, comprises the following steps of:

(a) feeding the olefinic gasoline to an etherification zone, where the reaction between said cut and methanol, is performed in order to obtain an effluent containing tert-amyl methyl ether, (b) feeding said effluent from step (a) to an extraction zone, wherein at least the major part of the unreacted methanol is extracted with water, and wherein a fraction in at least the major part of methanol, and containing the major part free of methyl tert-amyl ether, is recovered, (c) fractionating the aqueous extract obtained from step (b) in order to obtain ($\alpha$) a fraction of increased methanol content and decreased water content and ($\beta$) a fraction of decreased methanol content and increased water content, (d) at least partly recycling said fraction of increased methanol content to the etherification zone and at least partly recycling said fraction of increased water content to the extraction zone.

Said process provides for the upgrading of olefinic hydrocarbon cuts such as olefinic light gasolines, provided that they do not contain substantial amounts of $C_4$ hydrocarbon. These cuts may consist for example of a $C_5$–$C_7$ cut, particularly a catalytic cracking light gasoline containing essentially $C_5$, $C_6$ and $C_7$ hydrocarbons and in particular isoamylenes such as 2-methyl-1-butene, 2-methyl-2-butene, isohexenes such as 2,3-dimethyl-1-butene, 2,3-dimethyl-2-butene, 2-methyl-2-pentene, 2-methyl-1-pentene, 3-methyl-2-pentene and 2-ethyl-1-butene, and tertiary heptenes.

In order to obtain sufficient conversion rates, methanol is used in such an amount that the molar ratio of methanol to the sum of etherifiable olefins, i.e. essentially tertiary olefins of the cut, be at least equal to 1:1 and preferably comprised between 1:1 and 20:1, said ratio being more preferably from 2:1 to 6:1, at the inlet of the etherification zone.

The water amount used in the extraction zone is advantageously, by weight, from 0.4 to 3 parts (preferably 0.7–1.2 parts) per part of olefinic gasoline charge. In these conditions, the catalyst deactivation, over time, remains low. With water amounts lower than the above-mentioned proportions, a substantial deactivation of the catalyst is observed.

BRIEF DESCRIPTION OF THE DRAWING

The accompanying drawing represents a flowsheet illustrating one of the possible arrangements which are convenient for carrying out the process of the invention.

This flowsheet further shows that it is possible to etherify olefinic gasolines with methanol and to remove the methanol excess by mere washing with water, without the requirement of a distillation of the reactor effluent, which is an expensive operation.

In such a process, the olefinic gasoline is introduced through line (6) into the etherification zone, preferably consisting of two serially associated reactors (1) and (2), containing an acid catalyst such as ion-exchange resins, for example of the sulfonic type, such as the resin described in the U.S. Pat. No. 3,037,052.

Methanol is introduced through line (5) and admixed with gasoline before entering reactor (1). The effluent of the reactors is introduced through line (8) in a water extraction column (3) operating with hydrocarbon and water in countercurrent. The etherified gasoline, made free of methanol, is discharged through line (9) and fed to the motor fuel pool. Water is admitted into the extraction column through line (10). It is discharged, with its methanol content, from the column bottom and is fed, through line (11), to the distillation column (4) for separating methanol, which issues at the top and is recycled, through line (7) and valve $V_1$, to the inlet of the etherification zone.

In a preferred embodiment, at least a portion of methanol is recycled to reactor (2) through line (7) and valve $V_2$.

This flowsheet illustrates a particular embodiment of the invention. Various alternative embodiments may be considered without departing from the scope of the invention.

In particular, the etherification zone may be formed of a single reactor or more than two reactors and the unconverted methanol may be recycled into many of them.

Preferably, methanol is recycled, at least partly, into at least one reactor other than the first one.

The reactors of the etherification zone are so associated that at least two of them are in series; reactor associations wherein certain are in parallel may however be also considered.

The use of such a process, as illustrated in the accompanying drawing, for etherifying with methanol an olefinic gasoline mixture and a cracking $C_4$ cut, is not satisfactory.

As a matter of fact, it is observed that the conversion rate of tertiary olefins, isobutene, isoamylenes, isohexenes, progressively decreases with time and that the content of t-butyl alcohol (TBA) of the water used for washing the reactors effluent increases, thus correspondingly decreasing the yield of ether (MTBE and tert-amyl methyl ether-TAME).

These effects are attributable to the fact that the water used to extract methanol dissolves a part of the formed MTBE.

During the methanol distillation in column 4, MTBE issues at the top, driving therewith water by azeotropy. This MTBE and water, which are then introduced into the reactors, may contribute to decrease the performances of the process.

For the etherification of an olefinic gasoline, and $C_4$ cut mixture, the operation could be conducted as described in the U.S. Pat. No. 4,118,425, wherein the water used for washing the effluent is removed, but this would lead to a loss of MTBE and of methanol.

The authors of the invention have observed that, on the contrary, when etherifying with methanol an olefinic gasoline containing substantially no $C_4$ hydrocarbons and hence no isobutene, these disadvantages do not occur in continuous operating conditions.

This flowsheet of the process may be applied to unsaturated gasolines and particularly to steam-cracking gasolines and to catalytic cracking light gasolines.

The final distillation point of the catalytic cracking light gasolines may range from about 50° to about 150° C.

After treatment, these gasolines contain ethers and are essentially free of methanol.

EXAMPLES

The following examples illustrate the invention without limiting the scope thereof.

Example 1: (Comparative)

100 parts by weight of a catalytic cracking light gasoline of final distillation point equal to 130° C. and containing no $C_4$ hydrocarbons but essentially $C_5$, $C_6$ and $C_7$ hydrocarbons including 8% by weight of isoamylenes, 6.5% of isohexenes and 2.5% of isoheptenes and 80 parts by weight of $C_4$ cut containing 25% by weight of isobutene, are introduced through line (6) into reactor (1). 73.5 parts by weight of methanol are also introduced at the reactor inlet so that the molar ratio of methanol to the sum of the etherifiable isoolefins is equal to 4. This methanol consists on the one hand, of fresh methanol, fed through line (5), necessary to the formation of ethers and, on the other hand, of the methanol excess recycled through line (7) after distillation in column (4). The charge is introduced at 80° C. in reactor (1) at such a rate that the hourly volume velocity (VVH) be equal to 6. The effluent from this reactor is cooled in a heat exchanger, not shown, before being introduced at 70° C. into reactor (2), at such a rate that the VVH is equal to 3. The effluent from reactor (2) is washed with 250 parts of water in extraction column (3). The water, containing methanol, 1 to 1.5% of t-butyl alcohol (TBA) and 0.6% of MTBE, is distilled in column (4). Methanol and the MTBE-$H_2O$ azeotrope (containing 4% of water) are discharged at the top and recycled to reactor (s) through line (7).

The composition of the effluent from line (8) is given, versus time, in Table I.

After 300 hours of run, the formed amount of ethers is lower and the conversion rates of isobutene and isoamylene are also decreased.

The conversion of tertiary olefins is given in percents.

The product issuing from line (9) may be used directly for the formation of a gasoline mixture: its composition is the same as that of the effluent issuing through line (8), except that it contains substantially no methanol, or TBA.

Example 2

100 parts by weight of a light catalytic cracking gasoline, having the same final point and the same composition as in the preceding example, are introduced with 27.8 parts of methanol, into reactor (1).

The molar ratio of methanol to the sum of the etherifiable isoolefins is equal to 4.

The flow rate of charge, gasoline and methanol, is such that the VVH is equal to 6. The temperature at the reactor inlet is maintained at 80° C. The effluent from reactor (1) is cooled for being introduced at 70° C. into reactor (2) at such a rate that the VVH is equal to 3. The effluent is washed in column (3) with 130 parts of water. The methanol-containing water is distilled in column (4), giving at the top substantially pure methanol which is recycled through line (7) to reactor (1).

The composition of the effluent issuing through line (8) is given in table II. It is observed that this composition remains unchanged after 300 hours of run. In addition, it appears that the conversion rate of isoamylenes is higher than in example (1). The produced amount of ethers is also higher. The composition of the product obtained from line (9) is the same as that of the effluent from line (8), except that it practically contains no methanol.

TABLE I

| EFFLUENT | TIME IN HOURS | | |
|---|---|---|---|
| WEIGHT | 30 | 100 | 300 |
| $C_4$ | 61.1 | 62.2 | 62.7 |
| $C_5$ | 27.4 | 28.0 | 28.2 |
| $C_6$ | 26.9 | 27.3 | 27.6 |
| $C_7$ | 35.5 | 35.6 | 35.7 |
| MTBE | 29.5 | 27.5 | 26.7 |
| TAME | 8.2 | 7.3 | 7.0 |
| *$EtC_7$ | 4.9 | 4.4 | 4.0 |
| *$EtC_8$ | 1.3 | 1.2 | 1.0 |
| $CH_3OH$ | 58.5 | 59.7 | 60.2 |
| ABT | 0.15 | 0.25 | 0.3 |
| $iC_4$ conversion | 94.5% | 89% | 86.5% |
| $iC_5$ conversion | 70% | 63% | 60% |

*Symbols $EtC_7$, $EtC_8$, respectively mean ether with 7 and with 8 carbon atoms.

TABLE II

| EFFLUENT | TIME IN HOURS | |
|---|---|---|
| WEIGHT | 30 | 300 |
| $C_5$ | 26.6 | 26.70 |
| $C_6$ | 25.95 | 26.00 |
| $C_7$ | 35.25 | 35.85 |
| TAME | 9.32 | 9.20 |
| $EtC_7$ | 6.28 | 6.18 |
| $EtC_8$ | 1.66 | 1.58 |
| $CH_3OH$ | 22.74 | 23.60 |
| $iC_5$ conversion | 80% | 79% |

What is claimed as the invention is:

1. A process for upgrading an olefinic gasoline cut containing at least one tertiary olefin, having at least 5 carbon atoms per molecule, particularly isoamylenes, and which is essentially free of hydrocarbons of 4 carbon atoms, comprising the steps of:
    (a) feeding the olefinic gasoline cut to an etherification zone where said cut is reacted with methanol so as to obtain an effluent containing tert-amyl methyl ether,
    (b) feeding the effluent from step (a) to an extraction zone wherein at least the major part of the unreacted methanol is extracted with water and a fraction made free of at least the major part of methanol and containing the major part of tert-amyl methyl ether, is recovered,
    (c) fractionating the aqueous extract from step (b), so as to obtain only two fractions, ($\alpha$) a fraction of increased methanol content and decreased water content, and ($\beta$) a fraction of decreased methanol content and increased water content,
    (d) recycling at least a portion of the fraction of increased methanol content to the etherification zone and recycling at least a portion of the fraction of increased water content to the extraction zone.

2. A process according to claim 1, wherein the olefinic gasoline is a $C_5$–$C_7$ cut.

3. A process according to claim 1 wherein the methanol contained in the etherification effluent is countercurrently extracted with water.

4. A process according to claim 2 wherein the methanol contained in the etherification effluent is countercurrently extracted with water.

5. A process according to claim 1, wherein the etherification zone consists of at least 2 serially connected reactors.

6. A process according to claim 5, wherein the recycled methanol is at least partly recycled to the inlet of a reactor other than the first one.

7. A process according to claim 1, wherein the molar ratio methanol-etherifiable olefins, at the inlet of the etherification zone is from 1:1 to 20:1.

8. A process according to claim 1, wherein the molar ratio methanol-etherifiable olefins, at the inlet of the etherification zone is from 2:1 to 6:1.

9. A process according to claim 1, wherein the amount of water used in step (b) is from 0.4 to 3 parts by weight per part of olefinic gasoline charge.

10. A process according to claim 1, wherein the amount of water used in step (b) is from 0.4 to 1.2 parts by weight per part of olefinic gasoline charge.

11. In an etherification process for producing tert-amyl methyl ether comprising reacting a $C_5$ olefin with methanol in a first step to produce said tert-amyl methyl ether, and solvent extracting methanol in a second step, the improvement comprising employing as starting materials in the etherification reaction no $C_4$ hydrocarbons, employing water as the solvent, and fractionating resultant water/methanol mixture removed in said second step, said mixture being free of $C_4$ hydrocarbons, so as to obtain an essentially water-free fraction and an essentially methanol-free fraction, returning at least a portion of the essentially water-free fraction to the etherification step and returning at least a portion of the essentially methanol-free fraction to the extraction step, whereby resultant ethers withdrawn from the extraction step are essentially methanol-free.

* * * * *